United States Patent
Fulper et al.

(10) Patent No.: US 12,161,605 B2
(45) Date of Patent: Dec. 10, 2024

(54) METHOD TO RELIEVE STRESS IN CAPSULE SHELLS TO REDUCE PROPENSITY TO BREAK

(71) Applicant: R.P. Scherer Technologies, LLC, Las Vegas, NV (US)

(72) Inventors: Lester David Fulper, Clearwater, FL (US); Norton Hart, Clearwater, FL (US)

(73) Assignee: R.P. Scherer Technologies, LLC, Las Vegas, NV (US)

(*) Notice: Subject to any disclaimer, the term of this patent is extended or adjusted under 35 U.S.C. 154(b) by 0 days.

(21) Appl. No.: 16/467,408

(22) PCT Filed: Dec. 8, 2017

(86) PCT No.: PCT/US2017/065398
§ 371 (c)(1),
(2) Date: Jun. 6, 2019

(87) PCT Pub. No.: WO2018/107080
PCT Pub. Date: Jun. 14, 2018

(65) Prior Publication Data
US 2020/0069524 A1  Mar. 5, 2020

Related U.S. Application Data

(60) Provisional application No. 62/431,569, filed on Dec. 8, 2016.

(51) Int. Cl.
*A61K 9/48* (2006.01)
*A61J 3/07* (2006.01)
*F26B 21/00* (2006.01)
*F26B 21/04* (2006.01)
*F26B 21/08* (2006.01)
*F26B 21/10* (2006.01)
*F26B 21/12* (2006.01)
*F26B 3/02* (2006.01)

(52) U.S. Cl.
CPC ............ *A61J 3/077* (2013.01); *F26B 21/004* (2013.01); *F26B 21/04* (2013.01); *F26B 21/08* (2013.01); *F26B 21/10* (2013.01); *F26B 21/12* (2013.01); *A61K 9/4825* (2013.01); *F26B 3/02* (2013.01)

(58) Field of Classification Search
None
See application file for complete search history.

(56) References Cited

U.S. PATENT DOCUMENTS

| | | | |
|---|---|---|---|
| 4,497,157 A | 2/1985 | Durr et al. | |
| 4,506,453 A | 3/1985 | Shirley, Jr. et al. | |
| 4,539,060 A * | 9/1985 | Wittwer | A61J 3/072 156/275.1 |
| 4,720,924 A | 1/1988 | Hradecky et al. | |
| 4,917,885 A * | 4/1990 | Chiba | C08L 1/28 206/530 |
| 5,200,191 A * | 4/1993 | Steele | A61J 3/07 264/4.3 |
| 5,682,733 A | 11/1997 | Perrone | |
| 6,228,394 B1 | 5/2001 | Horhota et al. | |
| 6,967,026 B2 | 11/2005 | Hoshi et al. | |
| 8,181,425 B2 | 5/2012 | McCutcheon et al. | |
| 8,621,764 B2 | 1/2014 | Puckett | |
| 8,790,692 B2 * | 7/2014 | Wang | A61J 3/071 424/454 |
| 2004/0071808 A1 | 4/2004 | Peter et al. | |
| 2004/0247664 A1 * | 12/2004 | Dreja | B01J 13/02 424/452 |
| 2005/0025830 A1 | 2/2005 | Bruinewoud et al. | |
| 2007/0134289 A1 | 6/2007 | Burgermeister et al. | |
| 2014/0093606 A1 | 4/2014 | De Bock et al. | |
| 2014/0186437 A1 * | 7/2014 | Schoenhard | A61K 9/209 424/452 |
| 2015/0342892 A1 | 12/2015 | Vertommen et al. | |

FOREIGN PATENT DOCUMENTS

| | | |
|---|---|---|
| CA | 2452577 C | 4/2011 |
| CN | 1483393 A | 3/2004 |
| CN | 102283779 A | 12/2011 |
| CN | 103565647 A | 2/2014 |
| CN | 104672338 A | 6/2015 |
| CN | 103315976 B | 9/2015 |
| CN | 104991591 A | 10/2015 |
| CN | 105987587 A | 10/2016 |

(Continued)

OTHER PUBLICATIONS

Fulper et al (Evaluation of Capsule Cracking with Hygroscopic fills: An Alternative View. (2009):40-44 (Year: 2009).*
ISA Written Opinion for International Application No. PCT/US2017/065398; dated Mar. 29, 2018.
Fulper, David et al., "Influence of mechanical stress on the formation of cracks in two-piece capsules." Tablets & Capsules January (2010): 8-15.
Fulper, David et al., "Evaluation of Capsule Cracking with Hygroscopic Fills: An Alternative View" Tablets & Capsules September (2009): 40-44.

(Continued)

*Primary Examiner* — Jake M Vu
(74) *Attorney, Agent, or Firm* — Mendelsohn Dunleavy, P.C.

(57) ABSTRACT

A method of treating a soft or hard capsule shell to reduce or alleviate stress in the capsule shell. The method includes a step of heating at least a portion of the soft or hard capsule shell to a temperature above a glass transition temperature of the capsule shell but below a melt temperature of the capsule shell for a time sufficient to reduce internal stress in the capsule shell. The method can be used to reduce cracking of hard or soft capsule shells by application of the heat treatment to the filled capsule shells after fabrication and filling.

10 Claims, 7 Drawing Sheets

(56) References Cited

FOREIGN PATENT DOCUMENTS

| EP | 0014514 B1 | 6/1986 |
|---|---|---|
| EP | 2608769 B1 | 7/2013 |
| FR | 2361104 A2 | 3/1978 |
| GB | 2187703 A | 9/1987 |
| JP | 862-270160 A | 11/1987 |
| JP | 2007-521261 A | 8/2007 |
| JP | 2007-319672 A | 12/2007 |
| JP | 5355215 B2 | 5/2009 |
| JP | 2012-6861 A | 1/2012 |
| WO | 2014145699 A1 | 9/2014 |
| WO | 2018107019 A1 | 6/2018 |

OTHER PUBLICATIONS

International Search Report for International Patent Application No. PCT/US2017/065398; dated Mar. 29, 2018.
Extended European Search Report for corresponding European application No. 17878382.5; dated May 4, 2020.
Gullapalli, Rampurna Prasad. "Soft Gelatin Capsules (Softgels)." Journal of Pharmaceutical Sciences 99.10 (2010): 4107-4148.
Examination Report for corresponding Korean application No. 10-2019-7015395; dated Oct. 21, 2020 (15 pages).
Communication pursuant to Article 94(3) EPC for corresponding European application No. 17878382.5; dated Dec. 18, 2020 (5 pages).
First Office Action for corresponding Chinese application No. 201780070689.7; dated Mar. 5, 2021 (16 pages).
Examination Report for corresponding Russian application No. 2019113369; dated Mar. 18, 2021 (19 pages) Machine Translation.
Aguirre-Alvarez, G., et al. "The effect of drying temperature on mechanical properties of pig skin gelatin films El efecto de la temperatura de secado sobre las propiedades mecánicas de películas de gelatina de cerdo." CyTA—Journal of Food 9.3 (2011): 243-249.
Coppola, Mara, et al. "Phase Diagram of Gelatin Plasticized by Water and Glycerol." Macromolecular Symposia 273.1 (2008): 56-65.
Déjugnat, Christophe, et al. "Membrane Densification of Heated Polyelectrolyte Multilayer Capsules Characterized by Soft X-ray Microscopy." Advanced Materials 19.10 (2007): 1331-1336.
Köhler, Karen, et al. "Heat Treatment of Polyelectrolyte Multilayer Capsules: AVersatile Method for Encapsulation." Advanced Functional Materials 17.13 (2007): 2053-2061.
Cole, Ewart T. "Liquid filled and sealed hard gelatin capsules", Gattefossé Bulletin nr. 92 (1999): 1-12.
Office Action for corresponding Colombian application No. NC2019/0005238; dated Oct. 15, 2021 (14 pages).
Notice of Reasons for Refusal for corresponding Japanese application No. 2019-531045; dated Oct. 19, 2021 (8 pages).
Examination Report for corresponding Colombian application No. NC2019/0005238; dated May 14, 2021 (11 pages).
Reasons for Decision of Rejection for corresponding Korean application No. 10-2019-7015395; dated Apr. 23, 2021 (7 pages).
Technical Report for corresponding Brazilian application No. BR112019010069-5; dated Feb. 1, 2022 (9 pages) Machine Translation.
Notice of Reasons for Refusal for corresponding Japanese application No. 2019-531045; dated Feb. 8, 2022 (4 pages) Machine Translation.
Office Action for corresponding Colombian application No. NC2019/0005238; dated Feb. 23, 2022 (15 pages) Machine Translation.
Office Action for corresponding Israeli application No. 266695; dated Mar. 10, 2022 (3 pages).
Office Action for corresponding Indian application No. 201917019503; dated Feb. 22, 2022 (5 pages).
Examination Report No. 1 for corresponding Australian application No. 2017371180; dated Aug. 8, 2022 (3 pages).
Communication pursuant to Article 94(3) EPC for corresponding European application No. 17878382.5; dated May 30, 2022 (5 pages).
Examination Report No. 2 for corresponding Australian application No. 2017371180; dated Feb. 16, 2023 (3 pages).
1st Examination Report for corresponding Mexican application No. MX/a/2019/005956; dated Jan. 27, 2021 (8 pages) Machine Translation .
Technical Examination Report for corresponding Brazilian application No. BR112019010069-5; dated Dec. 6, 2022 (9 bages).
Office Action for corresponding Canadian application No. 3,045,127; dated Oct. 11, 2023 (3 pages).
Technical Examination Report for corresponding Brazilian application No. BR112019010069-5; dated May 2, 2023 (8 pages).
Office Action for corresponding Canadian application No. 3,045,127; dated Jun. 19, 2024 (4 pages).
Examination report based on New Zealand patent application No. 752946; dated Oct. 3, 2024 (7 pages).
Gennadios, Aristippos. "Soft Gelatin Capsules." Protein-based films and coatings. CRC press, 2002: 393-443.
Ahmed, J. "Thermal Properties of Gelatin and Chitosan." Glass Transition and Phase Transitions in Food and Biological Materials. Wiley, New York, 2017: 281-304.
Vassileva, Elena, et al. "New aspects of thermal treatment effects on gelatin films studied by microhardness." Macromolecular Chemistry and Physics 200.2 (1999): 405-412.
Fraga, Alicia N., and Roberto JJ Williams. "Thermal properties of gelatin films." Polymer 26.1 (1985): 113-118.
Felton, L. A., et al. "Physical-mechanical properties of film-coated soft gelatin capsules." International journal of pharmaceutics 127.2 (1996): 203-211.
Nazzal, S., and Y. Wang. "Characterization of soft gelatin capsules by thermal analysis." International journal of pharmaceutics 230.1-2 (2001): 35-45.
S. Fakirov, M. E. Cagiao, et al. Intern. "Melting of gelatin crystals below glass transition temperature: a direct crystal-glass transition as revealed by microhardness." J. Polymeric Mater (1999): 199-206.

* cited by examiner

METHOD TO RELIEVE STRESS IN CAPSULE SHELLS TO REDUCE PROPENSITY TO BREAK

BACKGROUND OF THE INVENTION

1. Field of the Invention

The present disclosure relates to a method of treating a capsule shell to relieve stress within the capsule shell and reduce the probability of cracking or damage to the shell during storage or handling.

2. Description of the Related Technology

Capsules are well-known dosage forms that normally consist of a shell filled with a fill material containing one or more pharmaceutical or other substances. Such capsules may have a soft or hard capsule shell.

Hard capsule shells are often manufactured using a dip molding processes. In this process the capsules are prepared by dipping mold pins into a solution of polymer, optionally containing one or more gelling agents and co-gelling agents. The mold pins are designed to mold a cap and a corresponding capsule body. The cap and capsule body are molded to provide a telescoping fit between the two parts. The mold pins are then removed, inverted, and dried to form a film on the surface. The dried capsule films are then removed from the molds and cut to the desired length. The telescoping fit caps are then assembled with the filled capsule body, and often a liquid banding solution is applied to bind the cap and body of the capsule together. The banding solution is allowed to dry, and the capsule is packaged. One example of this type of capsule and process is described in European patent no. 1 915 121.

U.S. Pat. No. 8,181,425 discloses an apparatus for sealing telescopically joined hard shell capsules by applying a sealing fluid uniformly to a gap in the capsule, providing an area of low pressure around the capsule to remove excess sealing liquid. The capsule is heated to cure the sealing fluid in order to seal the capsule.

Liquid Encapsulated Microspray Sealing is also used to make hard shell capsules. In this method, a water/ethanol microspray penetrates the cap and body portions of the capsule to lower the melting point in the sealing area of the capsule and the capsule is heated in air to complete the melting and fusion of the body and cap portions.

As the popularity of liquid-filled hard capsules (LFHCs) increases, there is a need to address the problem of cracking of the capsule shell. This can be particularly problematic when filling the capsules with hygroscopic fill materials that can cause the capsules to break. While breaks in capsules filled with powders can be a nuisance, breakage of LFHCs is unacceptable, since a single broken capsule can contaminate an entire package.

Capsules sometimes spontaneously break after banding while the bands are drying on trays. Breakage typically only occurs in the cap of the capsule. This problem can be linked to the dipping process used to make the capsules, which may results in the shoulder area of the capsules being the thinnest and, therefore, the weakest area of the capsule. Furthermore, the shoulder area of the cap coincides with the locking ring mechanism used to join the cap to the capsule body, whereby a tight interference fit between the capsule body and cap is used to prevent the capsules from popping open after closure. This interference fit at the locking ring causes additional stress at the shoulder area of the cap.

A significant number of capsules do not break at all. This is important because it indicates that there are capsule attributes that, if defined and controlled, could provide capsules that would be acceptable for use with hygroscopic fill materials. Previous studies determined that a difference in room humidity during manufacturing had an impact on the cracking rate of the capsules. This is relevant to capsules filled with hygroscopic materials since water in the capsule shell may cause cracking when exposed to a hygroscopic fill material due to water migration from the shell to the fill.

The existence of "stress raisers" has also been documented. "Stress raisers" are points or areas of the capsule shell where stress is concentrated. The existence of stress raisers in the capsule shell after the manufacturing process is complete, can increase the chance of a crack in the capsule shell. Cracks will occur when the concentrated stress exceeds the material's theoretical cohesive strength. (A material's actual threshold, or "fracture strength," is always lower than the theoretical value because of stress raisers.) Stress raisers can take the form of a sharp angle of a transition zone, a preformed hole or crack, or an interface between two different materials or two materials having different microstructures.

Three different possible solutions were previously studied to solve the cracking issue, as described by Fulper et. al. "Influence of mechanical stress on the formation of cracks in two-piece capsules", Tablet and Capsules, January 2010 and Fulper et. al. "Evaluation of capsule cracking with hygroscopic fills: An alternative view", Tablet and Capsules, September 2009. Each of these solutions provided some benefit, shed some light as to the causes of crack formation.

First, the shell thickness of the shoulder area can be increased. However, there is a point at which the thickness no longer has an impact on the amount of observed cracking. Second, reducing the relative humidity during the manufacturing process results in a lower water content gradient across the shell thickness, also reduces the incidence of cracking. However, reducing the relative humidity tends to cause the capsule shell to become more brittle, resulting in capsules that are more prone to breakage due to impact forces. Finally, changes in the shape of the locking ring can be used to reduce the number of, and impact of, "stress raisers" in the area of the locking ring. However, altering the design of the locking ring may negatively affect how securely the cap and body are affixed to each other.

Cracking issues also exist during the manufacture of soft elastic capsules since stress raisers may be present in the capsule shell upon drying the capsule after the filling process. Soft elastic capsules often include plasticizers to lower the melt or glass transition temperature of the capsule shell to prevent or reduce induced stress in the capsule shell. However, such plasticizers may render the capsule too soft and/or lower resistance to heat to an unacceptable extent thereby adversely affecting capsule performance. Additionally, plasticizers may have a negative impact on the stability of the capsule. As a result, there is a desire to reduce or eliminate the plasticizer from the capsule shell for these reasons. However, the presence of too little plasticizer may cause the capsule shell to become brittle and/or to fail at areas of high stress.

Thus, a system and methods for processing and/or manufacturing capsules are required to reduce crack formation in capsule shells and/or allow use of lesser amounts of plasticizers in the capsule shells.

SUMMARY OF THE INVENTION

In a first embodiment, the disclosure relates to a method of treating a soft or hard capsule shell. The method includes a step of heating at least a portion of the soft or hard capsule shell to a temperature above a glass transition temperature of the capsule shell but below a melt temperature of the capsule shell for a time sufficient to reduce internal stress in the capsule shell.

In the foregoing embodiment, the portion of the capsule shell may be heated to 2-10° C. below the melt temperature of the capsule shell, or to 2-7° C. below the melt temperature of the capsule shell, or 2-3° C. below the melt temperature of the capsule shell.

In each of the foregoing embodiments, the capsule shell may be a hard capsule shell. In this embodiment, the portion of the hard capsule shell may be the cap portion or the portion of the hard capsule shell may be the portion where the cap portion overlaps with the body portion of the capsule shell, or the portion of the hard capsule shell may be the entire capsule shell.

In each of the hard capsule shell embodiments, the heating step may be carried out immediately prior to closing the hard capsule shell by fitting the cap and body portions together, or after the hard capsule shell is closed by fitting the cap and body portions together.

In alternative embodiments, the capsule shell may be a soft elastic capsule shell. In this embodiment, the heat treating step may be carried out concurrently with drying the soft elastic capsule shell, or upon completion of drying of the soft elastic capsule shell. In each of the soft capsule shell embodiments, the portion of the soft elastic capsule shell may be the entire capsule shell.

In each of the foregoing embodiments, the time may be from 2 seconds to 24 hours, or from 12 hours to 24 hours, or from 2 seconds to 1 hour, or from 1 hour to 12 hours, or from 1 hour to 2 hours.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent or parameter disclosed herein is to be interpreted as being disclosed for use alone or in combination with one or more of each and every other component, compound, substituent or parameter disclosed herein.

It is also to be understood that each amount/value or range of amounts/values for each component, compound, substituent or parameter disclosed herein is to be interpreted as also being disclosed in combination with each amount/value or range of amounts/values disclosed for any other component(s), compounds(s), substituent(s) or parameter(s) disclosed herein and that any combination of amounts/values or ranges of amounts/values for two or more component(s), compounds(s), substituent(s) or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

In one embodiment, the present disclosure relates to a method to relieve stress in a capsule shell in order to reduce or prevent cracking of the shell. Without being bound by theory, it is believed that the flexible polymer chains located within capsule shell lose some molecular mobility during the shell formation process thereby locking the polymer chains into a more rigid conformation that is more brittle thereby increasing the propensity of the capsule to crack. It is postulated that heat treatment method of the present disclosure permits the polymer chains to relax into a less brittle state which is retained upon cooling thereby reducing the brittleness and internal stresses of the capsule shell. This is believed to reduce or prevent cracking of the treated capsules. The method is particularly useful for capsules filled with a hygroscopic fill material that would otherwise exhibit a greater tendency to crack.

During fabrication or manufacture of the capsule, cap portion and/or capsule body, stress risers may be created in the capsule shell that could lead to premature failure of the capsule. Materials such as gelatin used in the manufacture of capsules harden and contract during the drying process. The polymer chains become stressed because they cannot easily re-arrange after the shell reaches a particular level of dryness. Soft elastic capsules may typically include plasticizers to lower the melt or glass transition temperature of the capsule shell to prevent or reduce the aforementioned induced stress situations. However, such plasticizers may have a negative impact on capsule performance, or the stability of the capsule, and thus the reduction or elimination of the plasticizer from the capsule shell is desirable.

The terms "two piece capsule" and "hard shell capsule" are used interchangeably, and both refer to capsules that are manufactured using a two-piece system, wherein the two pieces are fit together, typically using an interference fit, after the fill material is inserted. Hard shell capsules typically have a plasticizer to gelatin or polymer ratio of from 0-0.25.

The present system and process is applicable to drying both hard shell capsules soft elastic capsules. The term "soft elastic capsule" may refer to gelatin-containing soft capsules, as well as other types of soft capsules that do not contain gelatin. Similar testing can be used for capsules that do not contain gelatin in order to determine the melting points and glass transition temperatures for a particular capsule formulation to be heat treated in the processes described below. "Soft capsule," "softgel capsule," and "soft elastic capsule" as used throughout the description refers to capsules that contain gelatin, or other polymer(s) in combination with an explicit plasticizer such as glycerin, or an intrinsic plasticizer such as water.

The "hardness" or "softness" of a capsule may be determined by a ratio of plasticizer to gelatin or other polymer. Hard capsules have a lower ratio, typically 0 to 0.25, and soft capsules have a higher ratio, which may typically range from 0.25 to about 0.7.

This method utilizes heat to relieve stresses induced during manufacture and/or drying of the capsule shell. Application of heat and optionally, controlled drying can be used to allow molecular arrangement of the shell to reduce stress risers and thereby reduce the propensity for capsule shell failure.

In a second application of this disclosure, the cap portion and capsule body of a two-piece capsule shell system are joined together by telescoping the body of the capsule into the cap of the capsule. The cap and/or body may include structure formed in or on the inner surface to provide an interference fit or locking mechanism for holding the cap portion and capsule body together once assembled. For example, indentations may be molded into the cap and body in a manner arranged to create a locking mechanism. Unfortunately, this locking mechanism or other "fit-interferences" can apply stress to the capsule shell, and particularly to the thinner section of the cap portion of the capsule that results in formation of stress risers (Fulper et. al. "Influence of mechanical stress on the formation of cracks in two-piece capsules", Tablet and Capsules, January 2010). Application of heat to the stressed areas of the capsule shell can provide stress relief to these areas of the capsule shell thereby reducing the propensity of the capsule shell to crack.

It is known that certain materials can cause stress risers to form in capsules as a dynamic of water migration that may cause capsules to crack. (Fulper et. al. "Evaluation of capsule cracking with hygroscopic fills: An alternative view", Tablet and Capsules, September 2009). Application of heat can be used to relieve stress conditions that develop as a result of water migration thereby reducing the propensity of such capsule shells to crack.

The system and methods of the present disclosure significantly reduce the number of capsules that unacceptably form cracks either through spontaneous cracking, or through mechanical impact forces. The methods of the disclosure employ heat to normalize/anneal/reduce internal stresses in the capsule shell by heating the capsule shell to a temperature above the glass transition temperature and preferably proximate to the melt temperature of the capsule shell material, typically after completion of the capsule manufacturing and filling process. The methods of the invention provide the additional advantage in soft elastic capsules of allowing reduction or elimination of plasticizers in the capsule shell.

Any suitable, conventional method of manufacturing and filling the capsules can be used in conjunction with the present methods. In one application of the present method, the capsules are first manufactured, dried, filled and, as necessary, assembled according to conventional methods. Heat is applied either during, or after capsule formation to allow molecular rearrangement of the capsule shell to a less brittle conformation thereby reducing or eliminating stress risers in the capsule shell.

Figure 1:
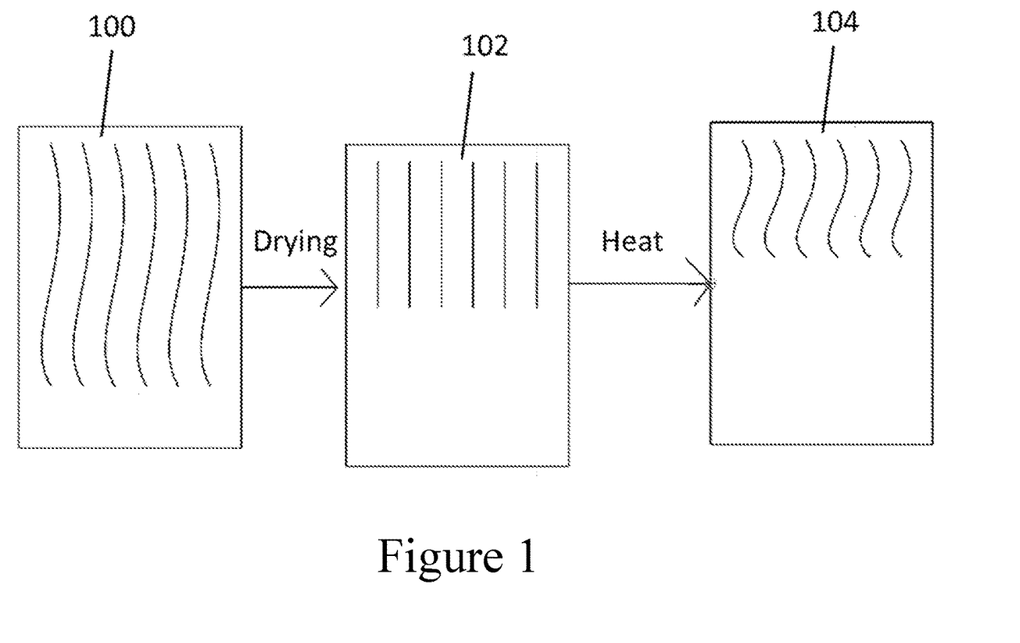
FIG. 1 is a schematic diagram of polymer chains in a capsule during the drying and heating process.

FIG. 1 schematically illustrates the postulated effect of applying heat to the capsule. When the film employed to make the capsule shell is wet, typically during the molding process, the polymer chains are flexible 100. As the film is dried, the polymer chains lose their flexibility, and become locked into a rigid conformation that is brittle and subject to cracking 102. Upon application of sufficient heat to the dried capsule shell material, molecular movement is allowed and the polymer chains relax into a less brittle state, which remains upon subsequent cooling 104.

In the present methods, an amount of heat is applied to heat at least a portion of the capsule shell to proximate the melt temperature of the capsule shell material.

Figure 2:
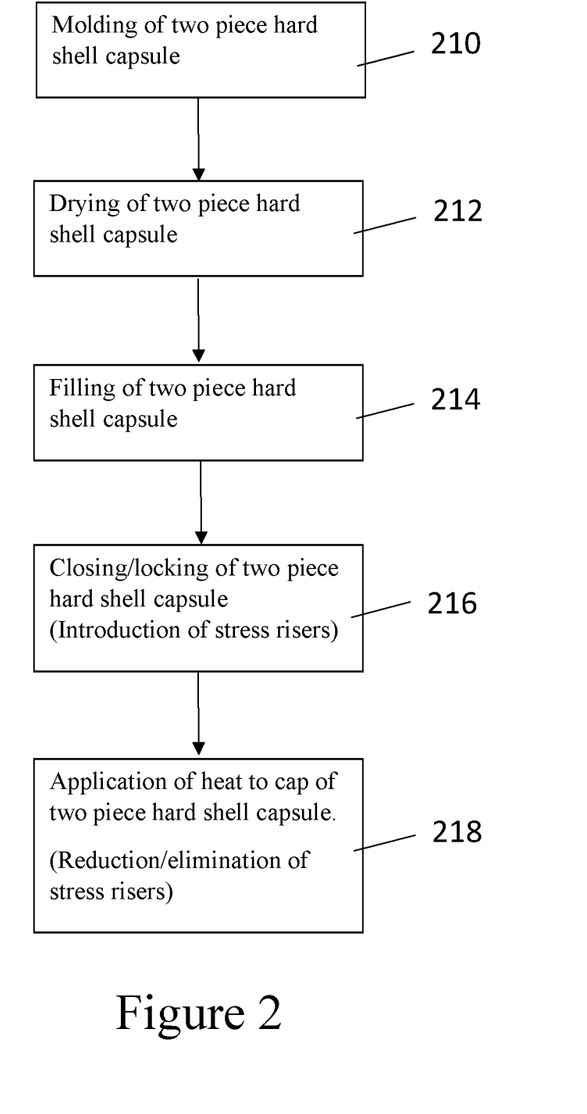
FIG. 2 is a flow diagram showing the steps of a method for manufacturing and treating a two-piece hard capsule according to a first embodiment of the disclosure

FIG. 2 is a flow chart depicting a first embodiment for the manufacture of hard shell capsules including the heat treatment step of the present disclosure. In the first step of the method of FIG. 2, the cap and body portions of a hard shell capsule are molded in step 210. The cap and body portions can be formed by any suitable conventional method. Preferably, the cap and body portions are made using a pin dipping method. An exemplary pin dipping method may include the following steps. First, a thermos-gelling solution is prepared. Capsule body pins and capsule cap pins are then dipped into the thermos-gelling solution to act as molds. The solution adheres to the dipped pins, which are then removed from the solution, and the solution remaining on the surface of the pins is dried in step 212. The capsule body and the cap portions may then be removed from the pins by gripping then and pulling them off the pins.

After the capsule cap and body portions are formed and removed from the pins, the hard shell capsule is filled in step 214 and the cap and body portions of the capsule are closed or locked by fitting the cap and body portions of the capsule shell together, preferably using an interference fit or locking mechanism in step 216. Suitable locking mechanisms are known in the art and include, for example, locking rings that are molded into the capsule cap and body portions and/or application of a banding solution to the interface or seam between the cap portion and the body portion of the capsule to bind the two portions together. In many embodiments the cap and body portions fit together as telescoping parts, i.e. the body portion slides a certain distance within the cap portion. As noted above, the drying step 212 and the closing or locking step 216 may introduce stress risers, or points in the capsule shell where cracking is more likely to occur.

Just prior to assembly of the capsule shell in step 216, or after the capsule shell is assembled, a heat treatment is applied to at least a portion of the capsule shell in step 218. The heat treatment step 218 may be applied immediately before closing and/or locking the capsule such that the effect occurs during closing of the capsule as a result of the capsule being at a temperature close to the critical stress relief temperature during closing. Alternatively, the heat treatment step 218 may be applied after closing the capsule. Preferably, the heat treatment is applied to the entire capsule, but it may also be applied to only the cap portion, or to a particular location of increased stress in the hard capsule shell such as the area of both the cap and body portions that overlap as a result of the telescoping assembly of the capsule since this is the part of the capsule shell that is subjected to stress as a result of assembly of the capsule shell using, for example, an interference fit.

Figure 3:
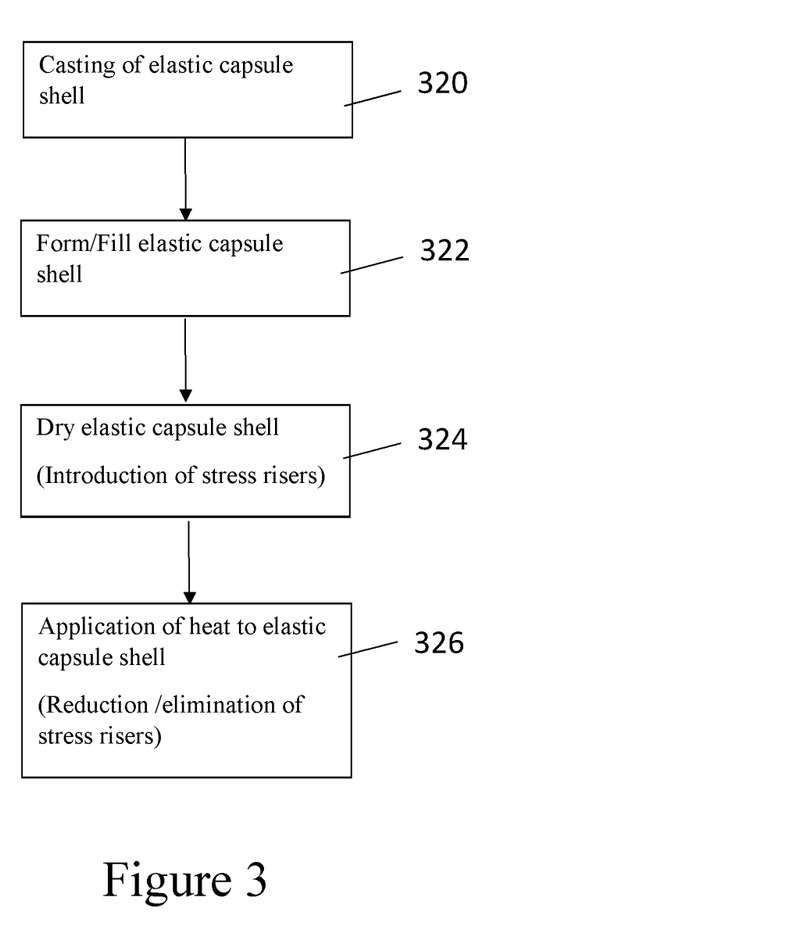
FIG. 3 is a flow diagram showing the steps of a method of manufacturing and treating an elastic form-filled capsule according to a second embodiment of the disclosure.

FIG. 3 is a flow chart depicting a method for the manufacture and filling of soft elastic capsule shells including the heat treatment of the present disclosure. The first step 320 of the method of FIG. 3 is the casting of the elastic shell capsules, which can be done using any suitable conventional method. The elastic capsules are then formed and/or filled in step 322 with a desired material. Once filled/formed, the elastic capsule shells are dried in step 324. Typically, stress risers are introduced during the drying step 324.

In one embodiment, the drying step 324 and/or capsule fabrication process does not heat the capsule shell material above the glass transition temperature of the capsule material. In this embodiment, the heat treating step would be useful to alleviate stress introduced during the drying step 324 and/or capsule fabrication process.

In another embodiment, the drying step 324 does not conclude at a temperature above the glass transition temperature of the capsule material and again the heating step of the invention would be useful to alleviate stress introduced during the drying step.

In yet another embodiment, the heat treating step can be employed for an elastic capsule shell made by any method which due to storage and/or handling subsequent to capsule drying requires alleviation of stress in the capsule material.

The heat treatment step 326 can be carried out either during the drying step 324, after drying is complete or a combination thereof. In this method, the elastic capsule shells are heated in step 326 to reduce or eliminate the stress risers. The heat treatment is preferably applied to the entire capsule shell, but may also be applied specifically to one or more locations of the capsule shell and particularly at one or more locations where increased stress is expected.

For either hard shell capsules, or soft capsules, the temperature to which the heat treated portion of the capsule shell is raised, should be selected to be the temperature at which stress relief will occur. This temperature is above the glass transition temperature for the capsule shell material and below the melt temperature of the capsule shell material. Preferably, the temperature is proximate to, but below the melt temperature of the material employed to form the capsule shell and typically at least 2° C. below the melt temperature of the material employed to form the capsule shell to avoid melting the capsule shell material. For example, the temperature of the heat treated portion of the capsule shell can be brought to a temperature 2-10° C. below the melt temperature of the material employed to form the capsule shell, or 2-7° C. below the melt temperature or 2-5° C. below the melt temperature, or 3-8° C. below the melt temperature or 3-6° C. below the melt temperature, or most preferably, 2-3° C. below the below the melt temperature of the material employed to form the capsule shell.

If a material to be treated has a very high melt temperature or no melt temperature, such a material should be heated to a temperature above its glass transition temperature in order to carry out the method of the present invention.

For most materials, the treatment temperature will fall within the rage of 22° C. to 120° C. It will be desirable to operate within OSHA's defined temperature safety limit and thus in some cases special apparatus having insulation or other safety features may be required to carry out the heat treatment step.

Figure 4:
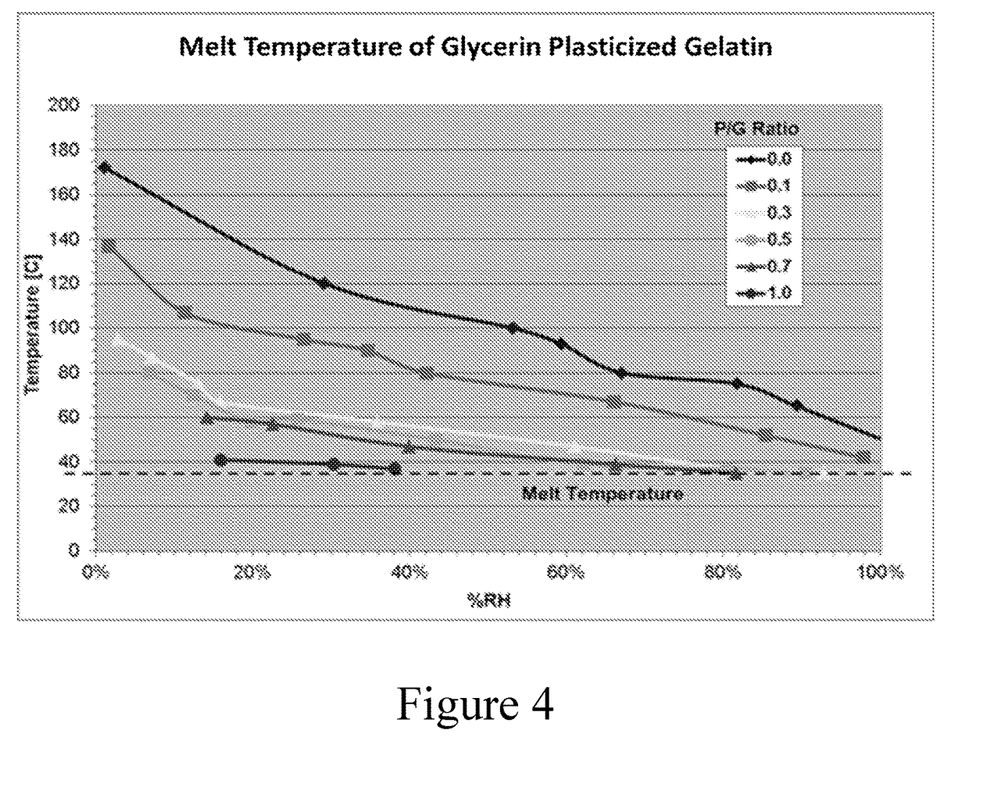
FIG. 4 is a graph showing the melt temperature of glycerin plasticized gelatin as a function of relative humidity during the manufacturing process.
Figure 5:
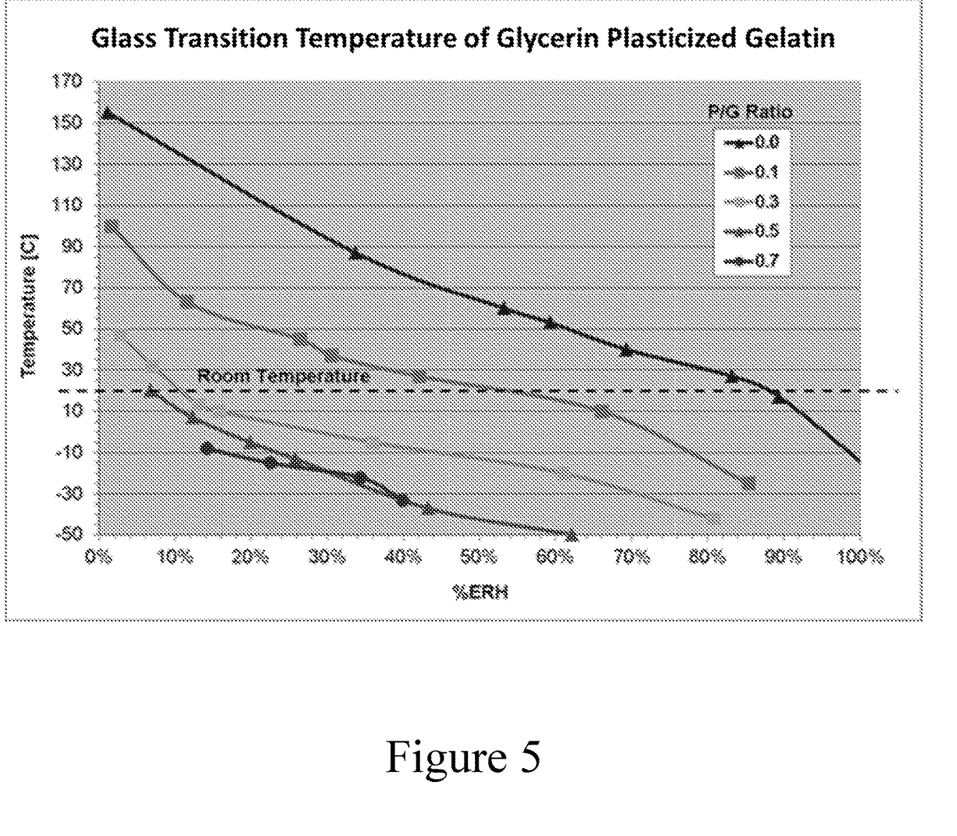
FIG. 5 is a graph showing the glass transition temperature of glycerin plasticized gelatin as a function of relative humidity during the manufacturing process.

FIG. 4 is a graph showing the melt temperatures of glycerin plasticized gelatin having various different ratios of plasticizers to gelatin. FIG. 5 is a graph showing the glass transition temperatures of glycerin plasticized gelatin having various different ratios of plasticizers to gelatin. These graphs are used to determine a suitable temperature for heat treating the capsule shell. Similar graphs for different polymers, or materials having different plasticizers and melt properties can be made by known methods. Although the preferred temperature ranges with respect to melt temperature are discussed above, any temperature between glass transition temperature and the melt temperature may be used.

The elevated temperature of the capsule shell is maintained for a time period that is sufficient to reduce internal stress in the capsule shell. The amount of time needed for treatment is dependent on the temperature selected, the capsule shell material, the type of equipment, and the type of heating technology. For temperatures closer to the melt temperature, the amount of time needed for heat treatment will be shorter, and for temperatures closer to the glass transition temperature the amount of time needed for heat treatment will be longer. If larger equipment, such as tumble dryers are being used, longer treatment times will be necessary. Infrared heating or microwaves can also be used to heat the capsule shell material.

Overall, the heat treatment will typically last for a few seconds up to 24 hours depending on the parameters selected. A skilled person can determine the necessary length of time by performing a hardness test and/or and impact test on the heat treated capsules to determine if they have acceptable properties. Thus, heating times can be from 2 seconds to 24 hours or from 10 seconds to 18 hours. Heating times can also be from 2 seconds to one hour or from 1-12 hours. In a preferred embodiment for use with soft capsules, the heat treatment is applied for 1-2 hours using a conveyor. If larger retaining equipment is used, such as tumble dryers, the heat treatment may last from 12-24 hours. For hard shell capsules, preferably the temperature is selected to decrease the processing time. As such a higher temperature close to the melting point may be selected, a result of which is that the heat treatment may be applied for as little as a few seconds.

The relative humidity during the heat treatment is preferably kept at less than 60%, and should be similar to or below the relative humidity at which the finished product will be stored.

Another advantage of the heat treatment method of the present invention is that it allows elastic capsule shell materials to be dried more quickly using accelerated drying processes which typically induce stress in the capsule shells. The present heat treatment process can be applied to such capsules subsequent to the accelerated drying step to alleviate stresses in the capsule shell created by accelerated drying. As a result, drying time may be significantly shortened when using the heat treatment step of the present process.

Another advantage of the heat treatment method of the invention is that it may permit use of lower amounts of plasticizers in the capsule shell since stresses induced during capsule manufacture can be alleviated by the heat treatment process. This is beneficial since the use of plasticizers also some disadvantages that can be reduced or avoided by reducing the amount of plasticizer needed in the capsule shell.

The following examples are illustrative, but not limiting, of the present disclosure. Other suitable modifications and adaptations of the variety of conditions and parameters normally encountered in the field, and which are obvious to those skilled in the art, are within the scope of the disclosure. The following examples illustrate the practice of the present disclosure in some of the preferred embodiments.

EXAMPLES

Example 1 (Impact and Hardness of Heat Treated Capsules)

The effect of heat treatment on the hardness and impact reaction of soft capsules was studied. For the control experiment, capsules containing a lipophilic fill material were placed in a weigh boat with a napkin on top at ambient conditions and allowed to dry. The use of a hydrophilic material is expected to give similar results.

Experimental capsules were subjected to accelerated drying with a heat treatment occurring during the drying. For this process, the temperature was ramped up from approximately 30° C. to approximately 48° C. for approximately 14 hours, after which the temperature was brought back down to 25° C. The relative humidity was also maintained at a high level throughout the experiment and ranged from 79% RH to 2% RH as the temperature increased.

The hardness of the samples was measured using a Bareiss Digitest Gelomat according to ASTM D2240 with a rate of 0.01 mm/sec for a period of 20 seconds. The impact reaction was measured by dropping a 237.6 g weight from different heights onto the capsule until the capsule broke. A salt cabinet humidity study was conducted to compare the impact and hardness results over a wide range of equilibrium relative humidities.

Figure 6:
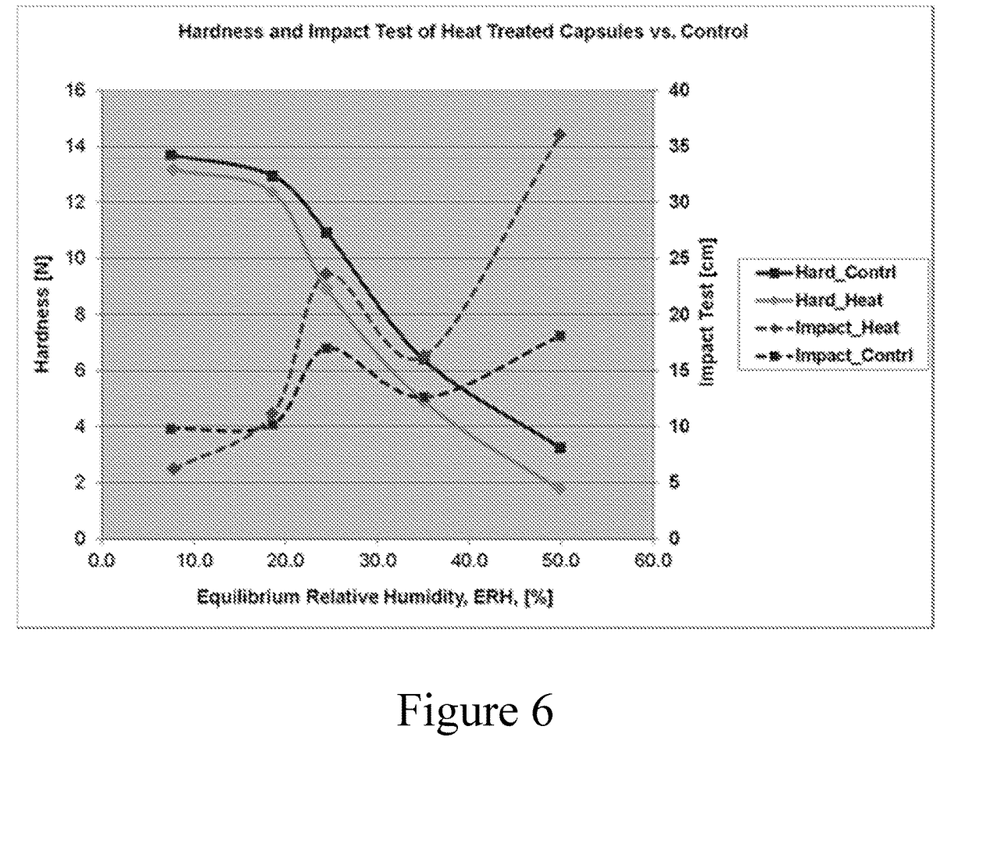
FIG. 6 is a graph showing hardness and impact strengths as a function of equilibrium relative humidity during manufacture of capsules treated according to an embodiment of the present disclosure compared to a control embodiment.
Figure 7:
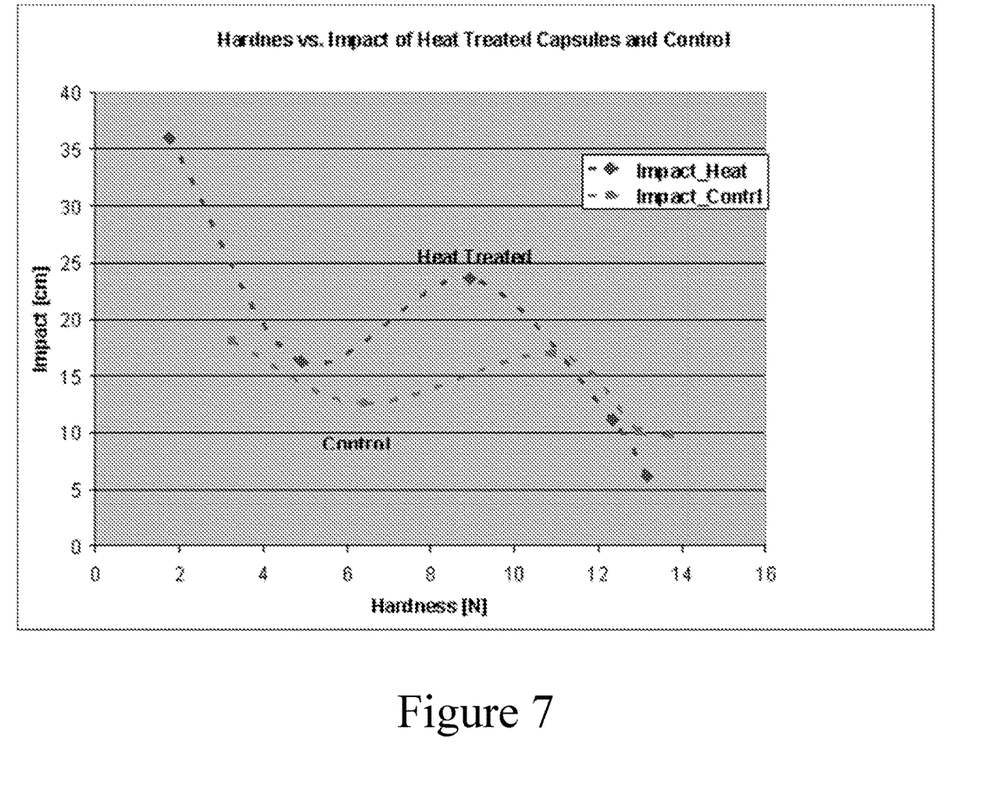
FIG. 7 is a graph showing impact strengths and hardness of capsules treated according to an embodiment of the present disclosure in comparison to a control embodiment.

FIG. 6 is a graph of the results of the hardness and impact tests over equilibrium relative humidities (ERH's) ranging from 10% to 50%. At all the ERH's, the impact results for the heat treated capsules was higher than the results for the control capsules. More importantly, as shown in FIG. 7, there is an optimal hardness between 7 N and 10 N where the impact results are much higher for the heat treated capsules than the control capsules. This is the range of hardness at which most capsules are considered to be acceptably dry.

The disintegration of the capsules was also tested, and there was no significant difference between the heat treated capsules and the control capsules.

It is to be understood, however, that even though numerous characteristics and advantages of the present disclosure have been set forth in the foregoing description, together with details of the structure and function of the disclosure, the disclosure is illustrative only, and changes may be made in detail, especially in matters of shape, size and arrangement of parts within the principles of the disclosure to the full extent indicated by the broad general meanings of the terms in which the appended claims are expressed.

What is claimed is:

1. A method to reduce propensity of cracking in a cap portion in a completed hard capsule shell formed of the cap portion and a body portion and comprising a locking mechanism comprising a structure formed in or on one or more of a surface of the cap portion or a surface of the body portion within an overlapping area for locking the cap portion and the body portion together, the locking mechanism forming a stressed area, wherein the completed hard capsule shell encapsulates a hygroscopic fill, comprising a step of:

heating the stressed area to a temperature above a glass transition temperature of the completed capsule shell but below a melt temperature of the hard capsule shell for a duration sufficient to reduce internal stress in the stressed area, wherein the hard capsule shell comprises gelatin and has a weight ratio of plasticizer to polymer of from 0 to 0.25, and the stressed area of the locking mechanism is heated to 2-10° C. below the melt temperature of the hard capsule shell, and the heating step is carried out after the hard capsule shell is closed by fitting the cap portion and the body portion together.

2. The method according to claim 1, wherein the heating step is carried out at a relative humidity of less than 60%.

3. The method according to claim 2, wherein the stressed area is heated to 2-7° C. below the melt temperature of the hard capsule shell.

4. The method according to claim 3, wherein the stressed area is heated to 2-3° C. below the melt temperature of the hard capsule shell.

5. The method according to claim 1, wherein the heating duration is from 2 seconds to 24 hours.

6. The method according to claim 5, wherein the heating duration is from 12 hours to 24 hours.

7. The method according to claim 5, wherein the heating duration is from 1 hour to 12 hours.

8. The method according to claim 2, wherein the heating duration is from 2 seconds to 1 hour.

9. The method according to claim 1, wherein the locking mechanism is selected from (i) locking rings which are molded into both the cap portion and the body portion of the capsule shell, and (ii) molded indentations of the cap portion and the body portion of the capsule shell.

10. The method according to claim 1, wherein the heating step heats the entire capsule.

* * * * *